(12) United States Patent
Barnes et al.

(10) Patent No.: US 11,819,289 B2
(45) Date of Patent: Nov. 21, 2023

(54) TRACKED POWERED DRILL ASSEMBLY

(71) Applicant: Medtronic PS Medical, Inc., Fort Worth, TX (US)

(72) Inventors: Milton F. Barnes, Fort Worth, TX (US); Thomas M. Meese, Louisville, CO (US); Michael Vu, Grand Prairie, TX (US); Vikram A. Garadi, Fort Worth, TX (US); Zachary S. Heiliger, Nederland, CO (US); Aayush Malla, Fort Worth, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 596 days.

(21) Appl. No.: 16/927,405

(22) Filed: Jul. 13, 2020

(65) Prior Publication Data

US 2020/0337785 A1    Oct. 29, 2020

Related U.S. Application Data

(62) Division of application No. 15/222,366, filed on Jul. 28, 2016, now Pat. No. 10,709,508.

(51) Int. Cl.
*A61B 34/20* (2016.01)
*A61B 17/16* (2006.01)
*A61B 17/17* (2006.01)
*A61B 90/00* (2016.01)
*A61B 17/00* (2006.01)

(52) U.S. Cl.
CPC ............ *A61B 34/20* (2016.02); *A61B 17/162* (2013.01); *A61B 17/1622* (2013.01); *A61B 17/1695* (2013.01); *A61B 17/1703* (2013.01); *A61B 2017/00398* (2013.01); *A61B 2017/00477* (2013.01); *A61B 2034/2051* (2016.02); *A61B 2034/2055* (2016.02); *A61B 2034/2072* (2016.02); *A61B 2090/3983* (2016.02)

(58) Field of Classification Search
CPC .......... A61B 34/20; A61B 2017/00477; A61B 17/162
See application file for complete search history.

(56) References Cited

U.S. PATENT DOCUMENTS

| 5,592,939 A | 1/1997 | Martinelli |
| 5,772,594 A | 6/1998 | Barrick |
| 5,871,493 A | 2/1999 | Sjostrom et al. |

(Continued)

FOREIGN PATENT DOCUMENTS

| CN | 100556370 C | 11/2009 |
| CN | 102892365 A | 1/2013 |
| JP | 2013524952 A | 6/2013 |

OTHER PUBLICATIONS

European Office Action regarding European Patent Application No. 17751527.7, dated Oct. 28, 2021.

(Continued)

*Primary Examiner* — David W Bates
(74) *Attorney, Agent, or Firm* — Carter, DeLuca & Farrell LLP (57) ABSTRACT

Disclosed is a system to engage one or more tools. In the system a drive shaft and collet may be assembled to engage and disengage, selectively, a plurality of tools. Further, a tracking device may be used to track a location of at least a portion of the tool.

9 Claims, 9 Drawing Sheets

(56) References Cited

U.S. PATENT DOCUMENTS

| | | | |
|---|---|---|---|
| 5,913,820 A | 6/1999 | Bladen et al. |
| 5,983,126 A | 11/1999 | Wittkampf |
| 6,081,741 A | 6/2000 | Hollis |
| 6,332,891 B1 | 12/2001 | Himes |
| 6,478,802 B2 | 11/2002 | Kienzle, III et al. |
| 6,546,277 B1 | 4/2003 | Franck et al. |
| 6,556,857 B1 | 4/2003 | Estes et al. |
| 6,718,194 B2 | 4/2004 | Kienzle, III |
| 6,725,082 B2 | 4/2004 | Sati et al. |
| 6,805,697 B1 | 10/2004 | Helm et al. |
| 6,887,245 B2 | 5/2005 | Kienzle, III et al. |
| 6,940,941 B2 | 9/2005 | Gregerson et al. |
| 7,001,045 B2 | 2/2006 | Gregerson et al. |
| 7,001,391 B2 | 2/2006 | Estes et al. |
| 7,011,661 B2 | 3/2006 | Riedel et al. |
| 7,106,825 B2 | 9/2006 | Gregerson et al. |
| 7,108,421 B2 | 9/2006 | Gregerson et al. |
| 7,130,676 B2 | 10/2006 | Barrick |
| 7,153,297 B2 | 12/2006 | Peterson |
| 7,188,998 B2 | 3/2007 | Gregerson et al. |
| 7,226,456 B2 | 6/2007 | O'Neil et al. |
| 7,314,048 B2 | 1/2008 | Couture et al. |
| 7,346,417 B2 | 3/2008 | Luth et al. |
| 7,477,926 B2 | 1/2009 | McCombs |
| 7,636,595 B2 | 12/2009 | Marquart et al. |
| 7,641,660 B2 | 1/2010 | Lakin et al. |
| 7,751,865 B2 | 7/2010 | Jascob et al. |
| 8,394,099 B2 | 3/2013 | Patwardhan |
| 8,545,510 B2 | 10/2013 | Christian et al. |
| 8,768,437 B2 | 7/2014 | Barrick |
| 8,842,893 B2 | 9/2014 | Teichman et al. |
| 8,961,536 B2 | 2/2015 | Nikou et al. |
| 8,974,460 B2 | 3/2015 | De la Fuente Klein et al. |
| 9,050,108 B2 | 6/2015 | Grinberg et al. |
| 9,060,794 B2 | 6/2015 | Kang et al. |
| 9,126,270 B2 | 9/2015 | Nishio et al. |
| 9,168,106 B2 | 10/2015 | Boyer et al. |
| 9,192,400 B2 | 11/2015 | Patwardhan |
| 9,283,048 B2 | 3/2016 | Kostrzewski et al. |
| 9,345,552 B2 | 5/2016 | Janik et al. |
| 10,709,508 B2 | 7/2020 | Barnes et al. |
| 2003/0023256 A1 | 1/2003 | Estes et al. |
| 2003/0163134 A1 | 8/2003 | Riedel et al. |
| 2004/0122460 A1 | 6/2004 | Shores et al. |
| 2004/0157188 A1* | 8/2004 | Luth .................. A61B 90/36 433/75 |
| 2004/0199072 A1 | 10/2004 | Sprouse et al. |
| 2005/0049564 A1 | 3/2005 | Fabian |
| 2006/0043684 A1 | 3/2006 | Barber et al. |
| 2008/0238677 A1 | 10/2008 | Blair et al. |
| 2009/0326540 A1 | 12/2009 | Estes |
| 2010/0228117 A1 | 9/2010 | Hartmann |
| 2011/0064978 A1 | 3/2011 | McGahan et al. |
| 2011/0263971 A1 | 10/2011 | Nikou et al. |
| 2012/0259337 A1 | 10/2012 | del Rio et al. |
| 2014/0276949 A1 | 9/2014 | Staunton et al. |
| 2015/0105833 A1 | 4/2015 | Simpson et al. |
| 2015/0313610 A1 | 11/2015 | Edwards et al. |
| 2016/0278802 A1 | 9/2016 | Cihak et al. |
| 2018/0028266 A1 | 2/2018 | Barnes et al. |
| 2018/0055519 A1 | 3/2018 | Barnes |

OTHER PUBLICATIONS

Office Action issued in Chinese Application No. 201780057572.5 dated May 26, 2021.
Office Action issued in Japanese Application No. 2019504079 dated Jun. 22, 2021.
"Medtronic Computer-Assisted Surgery" brochure, 10 pgs., 2005.
International Preliminary Report on Patentability dated Feb. 7, 2019 in corresponding International Application No. PCT/US2017/044174.
International Search Report and Written Opinion dated Jan. 2, 2018 in corresponding International Application No. PCT/US2017/044174.
Invitation to Pay Additional Fees dated Oct. 23, 2017 in corresponding International Application No. PCT/US2017/044174.
Korean Office Action regarding Korean Patent Application No. 10-2019-7005939, dated Jan. 26, 2022.
EESR No. 22202917.5 dated Jan. 26, 2023.

* cited by examiner

TRACKED POWERED DRILL ASSEMBLY

CROSS-REFERENCE TO RELATED APPLICATIONS

This application is a divisional of U.S. patent application Ser. No. 15/222,366, filed on Jul. 28, 2016. The entire disclosure of the above application is incorporated herein by reference.

FIELD

The present disclosure relates to a powered drill, and particularly to a powered drill that is configured to be tracked.

BACKGROUND

During selected procedures, a motor may be provided to power a drill motor that powers a tool, such as a tool that has a tool tip or working end. For example, the tool may be rotated at a selected velocity, such as about 100 rotations per minute (RPM) to about 10,000 RPM. The tool interconnected with the motor may be connected to a drive shaft configured to be powered by the motor to rotate. A procedure may then be carried out with the tool tip while rotating when powered by the motor.

During a selected procedure, such as a surgical procedure, the user of the tool (e.g. a surgeon) may need to rely solely on visual cues and experience for determining a location of the tool tip. During a procedure, at least a working end of a tool may be hidden from direct view or complete direct view of the user. Thus, an open experience may be required to properly perform a procedure.

SUMMARY

This section provides a general summary of the disclosure, and is not a comprehensive disclosure of its full scope or all of its features.

A powered drill may be provided to perform a procedure by a user. The powered drill may be powered in any appropriate manner, such as a pneumatic power, electrical power, or other appropriate power system to rotate at selected and/or selectable speeds including about 100 RPM to about 100,000 RPM, including about 75,000 RPM. The powered drill may power a tool for performing a procedure on a selected object, such as a human patient, or other appropriate subject. The powered drill may be powered to rotate the tool, such as for drilling, forming a burr hole, or the like.

During the procedure, the subject may have a predefined location or portion for having a procedure performed thereon. For example, a skull of a patient may be selected to have a burr hole formed therein. The location, size, etc. of the burr hole may be predefined during a planning procedure. The power drill may be operated to form the burr hole in the selected portion of the subject. Providing the powered drill to be tracked relative to an image of the subject, such as with a selected navigation system, may assist the user in determining or identifying the predetermined or selected location for performing a procedure on the subject. The navigation may also allow the user to see in real time a tracked location of the tool tip. Accordingly, the powered drill may have a tracking device associated (e.g., connected) thereto and a tool, including a working end, tracked relative to the tracking device.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
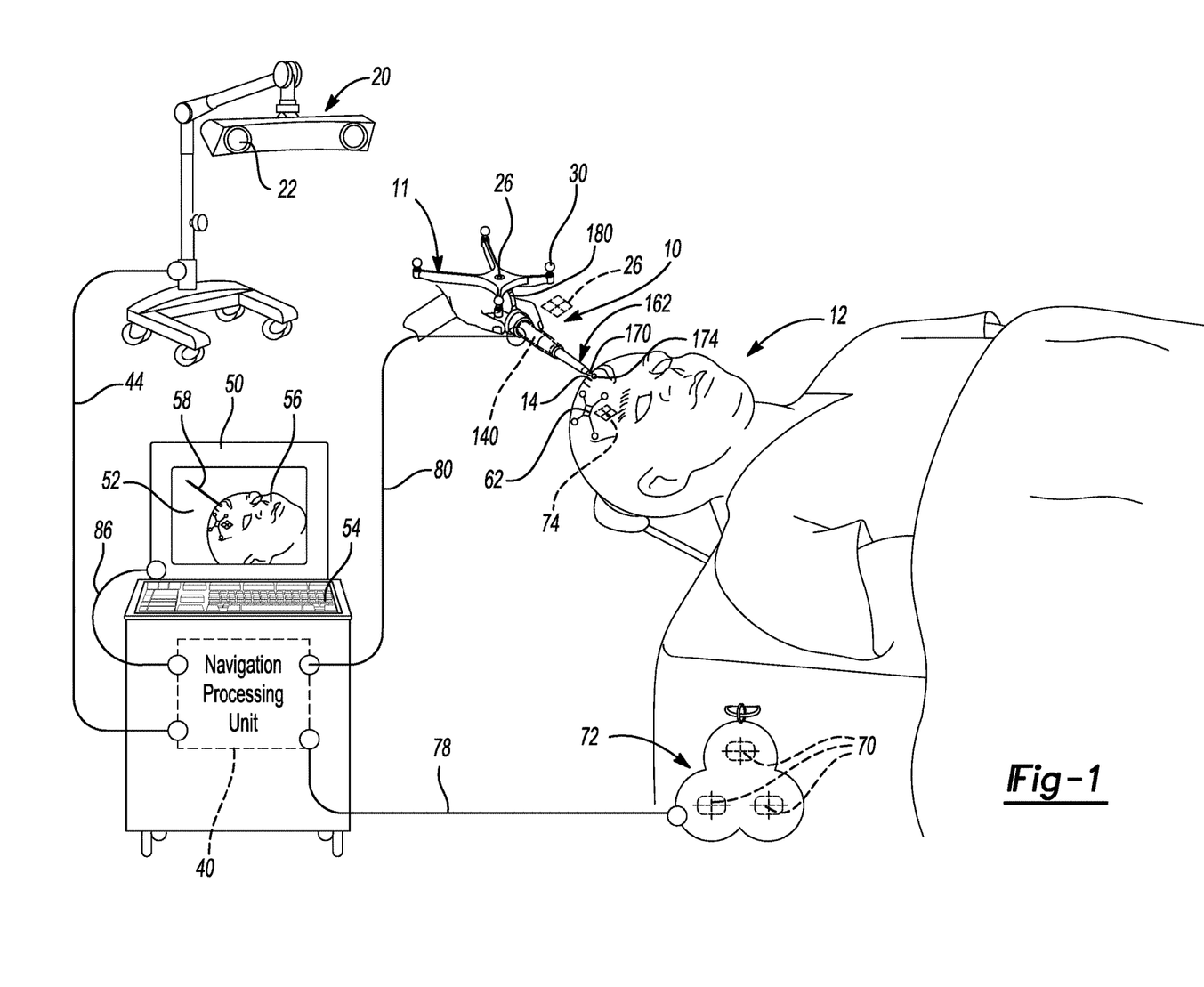
FIG. 1 is an environment view of a tracked motorized assembly.

FIG. 1 is an environmental view of an instrument, such as a powered drill assembly 10, being used by a user 11, to perform a procedure on a subject (e.g. a patient) 12. The powered drill assembly 10 may be powered to rotate a motor and/or a tool at selected and/or selectable speeds including about 100 RPM to about 100,000 RPM, including about 200 RPM to about 75,000 RPM. In various embodiments, the powered drill assembly 10 may include a powered dissection tool 170 for performing a select procedure, such as forming a burr hole in a cranium 14 of the patient 12. It is understood, however, that the powered drill assembly 10 may be used for performing other procedures such as a removal of material relative to a nasal cavity of the subject 12 or other appropriate procedure. Further, the powered drill assembly 10 may be used for various other procedures, including spinal procedures, orthopedic procedures, etc. For example, the powered drill assembly 10 may be operated to remove a portion of a vertebra in a selected procedure, including a laminectomy procedure or other appropriate spinal procedure. Further, it is understood that the powered drill assembly 10 may be used to perform a procedure on a non-living subject such as to drill a hole in an airframe, an automotive frame, or the like. Accordingly, the powered drill assembly 10 is not required to be used with a living subject, such as a human patient.

The powered drill assembly 10 may include a motorized drill that is tracked and/or navigated relative to the subject 12 according to various systems and/or procedures. For example, a tracking system, as discussed further herein, may include a tracking device 26 that may be connected to the powered drill assembly 10 to track a location of a tool relative to the subject 12, such as the cranium 14. Appropriate tracking systems include those disclosed in U.S. Pat. No. 8,842,893, incorporated herein by reference. It is understood that image data may be acquired of the subject 12 to create images, as discussed herein. To acquire the image data imaging systems (not illustrated) may be used prior to beginning a procedure or after a procedure has begun, the procedure may include operation of the powered drill 10. The imaging systems may include those disclosed in U.S. Pat. Nos. 7,188,998; 7,108,421; 7,106,825; 7,001,045; and 6,940,941; all of which are incorporated herein by reference. Other possible imaging systems can include C-arm fluoroscopic imaging systems which can also generate three-dimensional views of the patient 12.

The tracking system may be a part of a navigation system to assist in performing selected procedures, such as a surgical procedure on the subject 12, and may include those as generally known in the art. For example, navigation systems may include those as disclosed in U.S. Pat. Nos. 5,772,594; 5,913,820; 5,592,939; 5,983,126; 7,751,865; and 8,842,893 and those disclosed in U.S. Pat. App. Pub. Nos. 2004/0199072 and 2010/0228117, all incorporated herein by reference. Tracked locations may be displayed on images or relative to images due to registration of a location of a subject or real space to an image space, also as disclosed in the U.S. patents and publications as incorporated above. Further, tracking systems may include the Stealth Station® Trion™ tracking system, Stealth Station® Ion™ tracking system, Stealth Station® S7® tracking system, and AxiEM™ tracking system, all sold by Medtronic Navigation, Inc.

The tracking systems may include various features such as an optical tracking systems, EM tracking systems, ultrasonic tracking systems, or the like. Nevertheless, as illustrated in FIG. 1, for example, a tracking system may include one or more localizers such as an optical localizer 20 that includes one or more cameras 22 that may detect or "view" the tracking device 26 connected to the power drill 10. The localizer 20 including the cameras 22 may emit a selected radiation, such as infrared radiation, that is reflected by one or more trackable portions 30 that are associated with the tracking device 26. The trackable portions 30 may be viewed by the cameras 22 and a signal may be transmitted to a navigation processor unit 40. The navigation processor unit 40 may include various features, such as a navigation probe interface (NPI), as discussed further herein. The navigation processor unit 40 may also include a coil array controller (CAC) for various types of tracking systems. Various features such as the NPI, the CAC, or other portions may be provided as separate units from the navigation processor unit 40 or separate modules for interacting with various portions of the navigation system, as is generally known in the art.

Nevertheless, the localizer 20 may communicate with the navigation processor unit 40 via a selected communication line 44. The communication line 44 may be a wired or a wireless communication with the navigation processor unit 44. The navigation processor unit 40 may communicate with a selected system, such as a workstation, a terminal, or the like that includes a display system or display module 50 having a display screen 52 and one or more user inputs 54. The user inputs 54 may include a keyboard, a mouse, a touch screen, or other tactical input. Further inputs may also include a foot switch, verbal inputs, visual inputs, or the like.

The display device 50 may display an image 56 of a portion of the subject 12, such as the cranium 14. The image 56 may be based on or generated with image data acquired with an imaging system as discussed above. Displayed relative to the image 56 and/or superimposed on the image 56 of the patient 12 may be an icon 58 that displays a location of the powered drill assembly 10, including the tool 170, relative to the subject 12. The position of the powered drill assembly 10, or a portion thereof, relative to the subject 12 may be determined by registering the powered drill assembly 10 relative to the subject 12 and thereafter tracking the location of the powered drill assembly 10 relative to the subject 12. Various registration and tracking techniques are known, such as those discussed above, and are not repeated here. Nevertheless, a patient tracking device 26 may be associated with the patient 12, such as connected to the cranium 14.

Tracking systems may also include electromagnetic tracking systems including an electromagnetic tracking array, such as a coil array 70. The coil array 70 may include one or more coil elements 72 that emit and/or receive an electromagnetic signal from an electromagnetic (EM) tracking devices such as a patient tracking device 74 associated and/or connected to the patient 12 or a tracking device 76 connected to the power drill 10. The coil array 70 may communicate with navigation processes unit 40 via a communication line 78 similar to the communication line 44 from the localizer device 20 to the navigation processor unit 40. Further, each of the tracking devices may communicate with the navigation processing unit 40 via selected communication lines such as communication line 80 so that a position of the selected tracking devices, including tracking device 20 and tracking device 62 may be determined with a navigation processing unit 40. It is understood that one or more than one tracking system may be used simultaneously and/or serially during the selected procedure.

As discussed above, registration of the powered drill assembly 10 relative to the subject 12 may be made at a selected point in a procedure. The image 56 may then be displayed on the display screen 52 and a tracked location of the powered drill assembly 10 may be displayed as the icon 58 relative to the image 56. The icon 58 may be superimposed on the image 56 to display a location of at least a selected portion of the powered drill assembly 10, such as a distal end, of the tool 170 powered by the powered drill assembly 10. The location may be determined and/or calculated by the navigation processing unit 40 and communicated to the display device 50 via a selected communication line, such as communication line 86. The communication line 86 may be a wired or wireless or other appropriate communication line. Further, it is understood that the navigation processor unit may include various features such as a selected processor (e.g., an application specific integrated circuit (ASIC), general purpose processor or the like). The navigation processor unit 40 may also include a memory system (e.g. non-transitory memory systems including spinning hard disks, non-volatile solid state memory, etc.) that includes selected instructions, such as those to perform the tracking, registration, superimposing of the icon 58 on the image 56, or the like. Therefore the determined location of the powered drill assembly 10 (for example the selected portion of the powered drill assembly 10, as discussed further herein), may be displayed relative to the subject 12 by the icon 58 relative to the image 56. The user 11 may then be able to view the display device to view and/or comprehend the specific location of the selected portion of the powered drill assembly 10 relative to the subject 12 by viewing the display 52.

Figure 2:
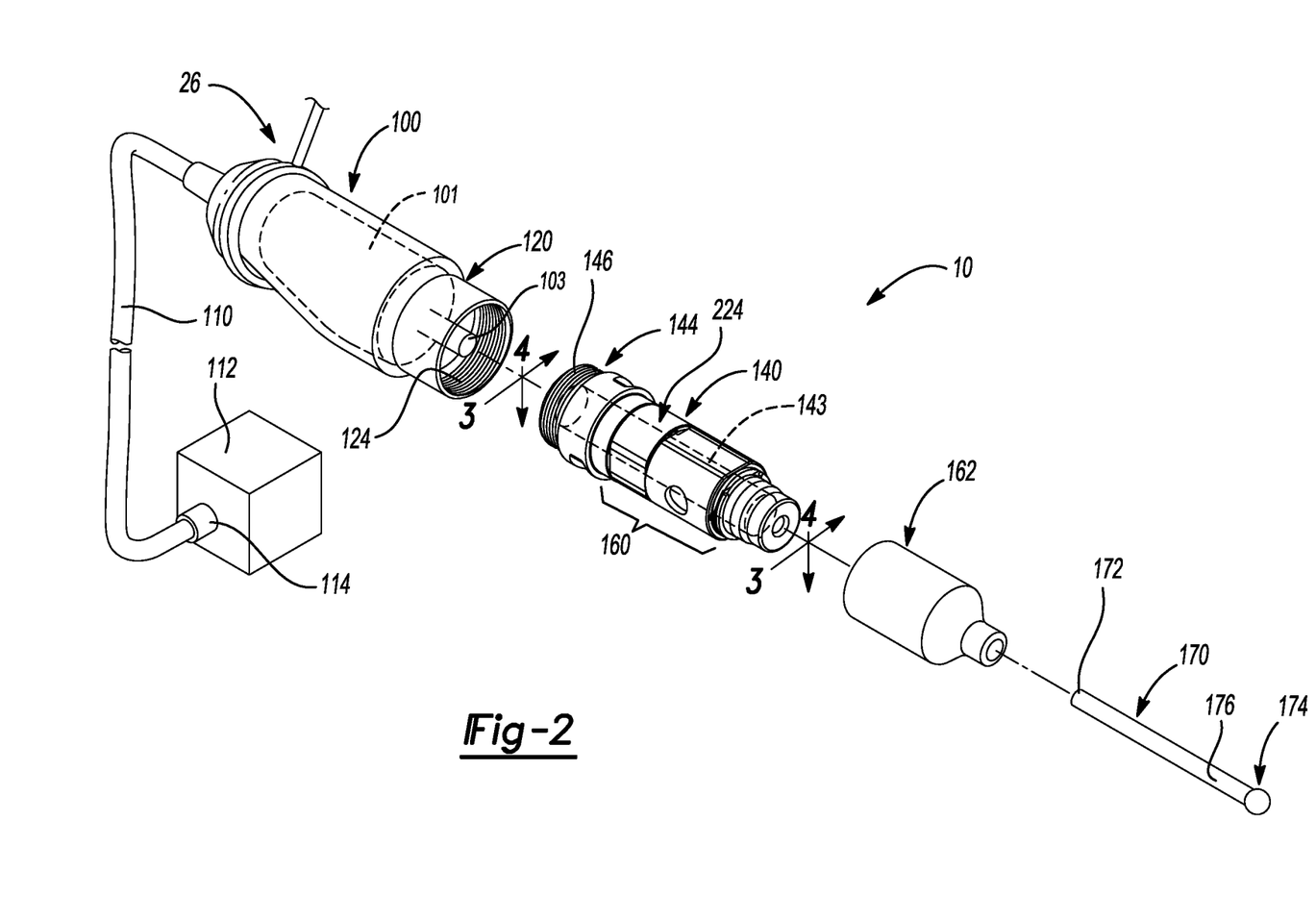
FIG. 2 is an exploded schematic view of a powered drill assembly.

With additional reference to FIG. 2 the powered drill assembly 10 may include various components which may include a motor housing 100 of a motor assembly or component. The motor component may include an appropriate motor component such as the LEGEND MR7® and/or LEGEND EHS STYLUS® motor systems, sold by Medtronic, Inc. The motor component may include a motor 101 that is powered such as a pneumatic powered, such as the LEGEND MR7® motors although other power motors or drives may be used such as electric power motors LEGEND EHS STYLUS® motors. The motor 101 may drive a motor drive shaft 103.

The power may be provided to the motor assembly via a power line 110 that is connected with a power source 112 via a connector 114. The power source 112 may be any appropriate power source such as the IPC® integrated power system, sold by Medtronic, Inc. It is understood, however, that the motor component may be any appropriate motor assembly such as one powered by electronic power, or other appropriate power supply. Therefore, the pneumatic power drill is not intended to limit the subject disclosure or the pending claims. Moreover, the motor component may include those disclosed in U.S. Pat. No. 7,011,661 or 7,001,391, both incorporated herein by reference.

The motor housing 100 may include a connector 120 that has a threaded portion, such as an internal thread 124. The threaded portion 124 may threadably engage a collet assembly 140 that includes a driveshaft 143 (within a collet housing 220 (FIG. 3)). The collet drive shaft 143 may engage to be driven by the motor driveshaft 103. The collet drive shaft may then engage the tool 170 and or a secondary drive shaft, such as a shaft within an attachment.

The collet assembly 140 may include a motor housing connector 144 that has external threads 146 to engage the internal threads 124. Thus, the collet assembly 140 may threadably and securely engage the motor body and housing 100. Generally, the collet assembly 140 is axially and rotationally secured relative to the motor housing 100 with the threaded engagement and/or other appropriate connections. The threaded connection may form at least a first connection or locking system of the collect assembly to the motor housing and the tracking device 26. Other appropriate connections to secure the collet 140 to the motor housing 100 both axially and rotationally may also be used, such as brazing, bayonet locking systems, etc. The first locking system, however, rotationally and axially rigidly fixes the collet 140 to the motor housing 100. In securing the collet assembly 140 to the motor housing 100 the collet drive shaft may be driveably connected to a motor drive shaft (not specifically illustrated), thus when the motor is powered the collet drive shaft may rotate to drive the tool 170.

The powered drill assembly 10 may further include an attachment connection portion 160. The attachment connection portion 160 may allow a connection of an attachment 162. The attachment 162 may include a surface and/or bearing portion that assists in supporting the tool 170. It is understood by one skilled in the art that the tool 170 may include more than one tool member and may include a kit of tools. The attachment 162 may not be required to be connected to the collet 140, but may be selected for various tools. Further, the attachment 162 may include various additional features, such as allowing for an angled connection of the tool 170 to the drive shaft assembly. The tool 170 may be any appropriate selected tool such as a drill bit, a burr, a driver, etc. Further, the tool 170 may include a drive shaft engaging end 172 (that may be a proximal end), a working end 174 (that may include a driver, bit, etc.), and a shaft 176 extending between the two ends 172, 174.

Figure 3:
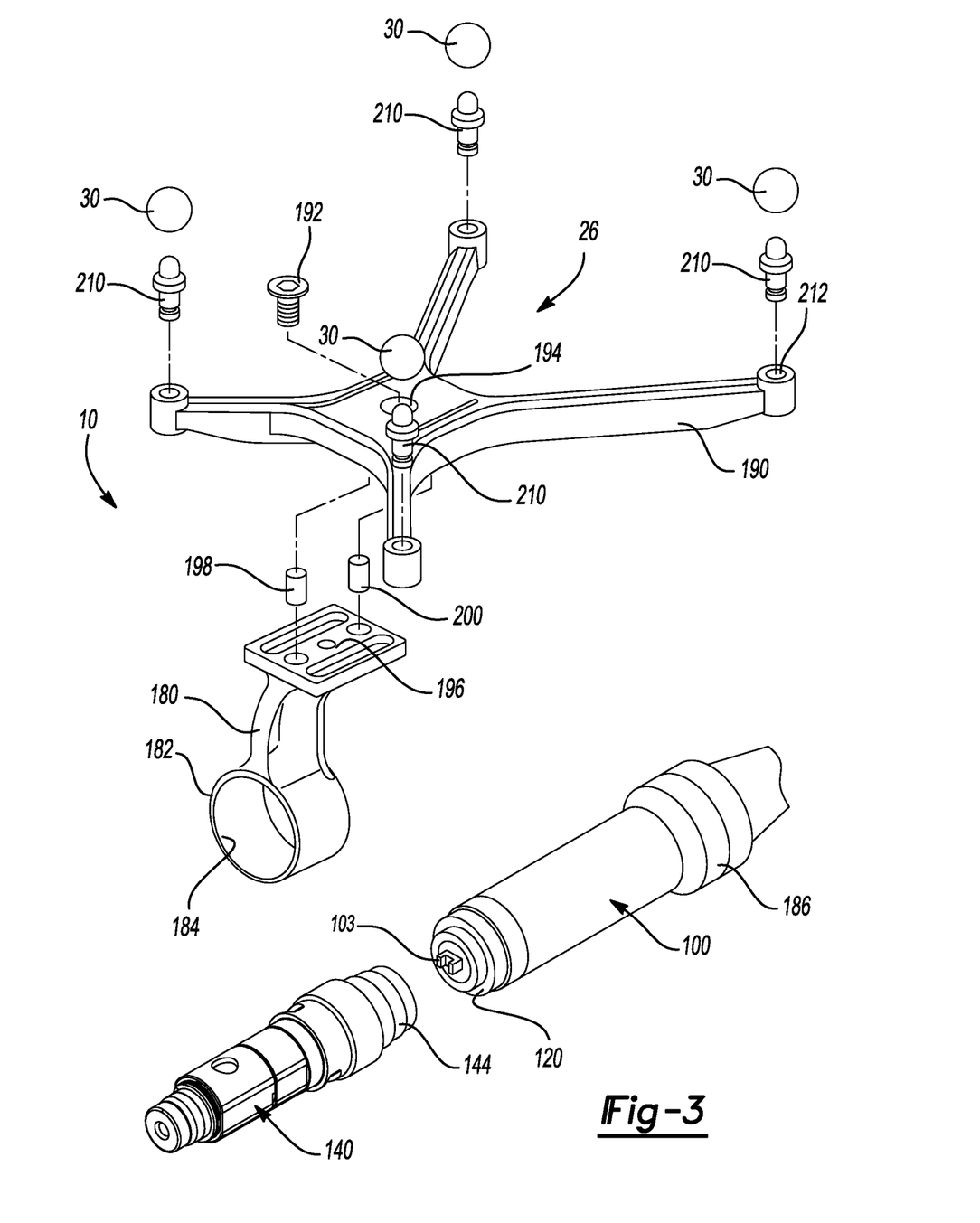
FIG. 3 is an exploded view of a tracking assembly and the powered drill assembly.

With additional reference to FIG. 3, the powered drill assembly 10 is illustrated in further detail. The powered drill assembly 10 may include the drill motor housing 100 and the connection 120. Further, as discussed above, the tracking device 26 may be connected to the drill motor housing 100 or form a part of the housing. The tracking device 26 may be connected to the drill motor housing 100 with a connector or stand 180. The connector 180 may include a ring or annular member 182 that includes an internal circumference or surface 184 that slides over and fixedly and rigidly engages an external surface 186 of a portion of the drill motor housing 100. The connection of the internal surface 184 with the external surface 186 may fixably engage the connector 180 with the motor housing 100 both axially and/or rotationally. In other words, the connector 180 prevents rotation and/or axial motion of the tracking device relative to the motor housing 100.

An array member 190 may be connected to the connector 180 with various fixation portions. For example, a fixation screw 192 may be threaded through a through bore 194 into a threaded receiving bore 196 in the connector 180. Additional anti-rotation or fixation pins 198 and 200 may be provided to interconnect the array 190 with the connector 180. Therefore, the array 190 may be fixably and rigidly connected, both axially and rotationally, relative to the connector 180. This allows the array 190 to be fixably connected to the motor housing 100 both axially and rotationally.

The array, having trackable portions 30 thereon, is fixedly and rigidly connected to the housing 100. This allows for accurate tracking of the powered drill assembly 10, as discussed herein. Further, the connector 180 may be offset or have a curve to assist in placing the trackable portions away from the operating portion of the powered drill 10 and in view of the localizer 20.

Further, as discussed above, various trackable markers or portions 30 may be interconnected with the array 190. The markers 30 may be passive reflectors and/or active emitters to be viewed by the localizer 20. The markers 30 may be connected with the array 190 via one or more pins 210. The pins 210 may be fixed into the array 90 in one or more bores 212. The bores may receive the pins 210 via a taper fit, an interference fit, a threaded connection, an adhesive, or other appropriate fixation. The trackable portions 30 may then be fixed to the pins 210, such as via a snap or interference fit. In this way the trackable portions 30 are fixed relative to the array 190 through the pins 210 both axially and rotationally.

The trackable portions 30 may be portions that are viewed with cameras 22. It is understood, however, that the trackable portions may be EM tracking devices 76 that are tracked with the EM localizer 70. Thus, the tracking device 26 and/or the tracking device 76 may be fixed to the motor housing 100. Further, it is understood that other fixation mechanisms may be provided to fix the tracking devices 26, 76 to the motor housing 100. For example, the tracking device 76 may be formed in or to the housing 100 such as by molding and/or welding. In other words, the tracking device 26, 76 may be formed as one unitary piece with the housing 100. Further, the connector 180 may be formed as one unitary piece with the housing 100.

By fixing the tracking device 26, 76 both axially and rotationally relative to the drill motor housing 100 a location (including both a XYZ position and at least one or yaw, pitch and roll orientation) may be determined. The tracking system, including the navigation processor unit 40 may receive a signal from a selected localizer regarding the tracking device 26 (and/or the tracking device 76) to determine the location of the motor housing 100. As discussed herein the position of various portions connected to the motor housing 100 may therefore be determined based upon a known location of portions connected to the motor housing 100 relative to the tracking device 26.

Figure 4:
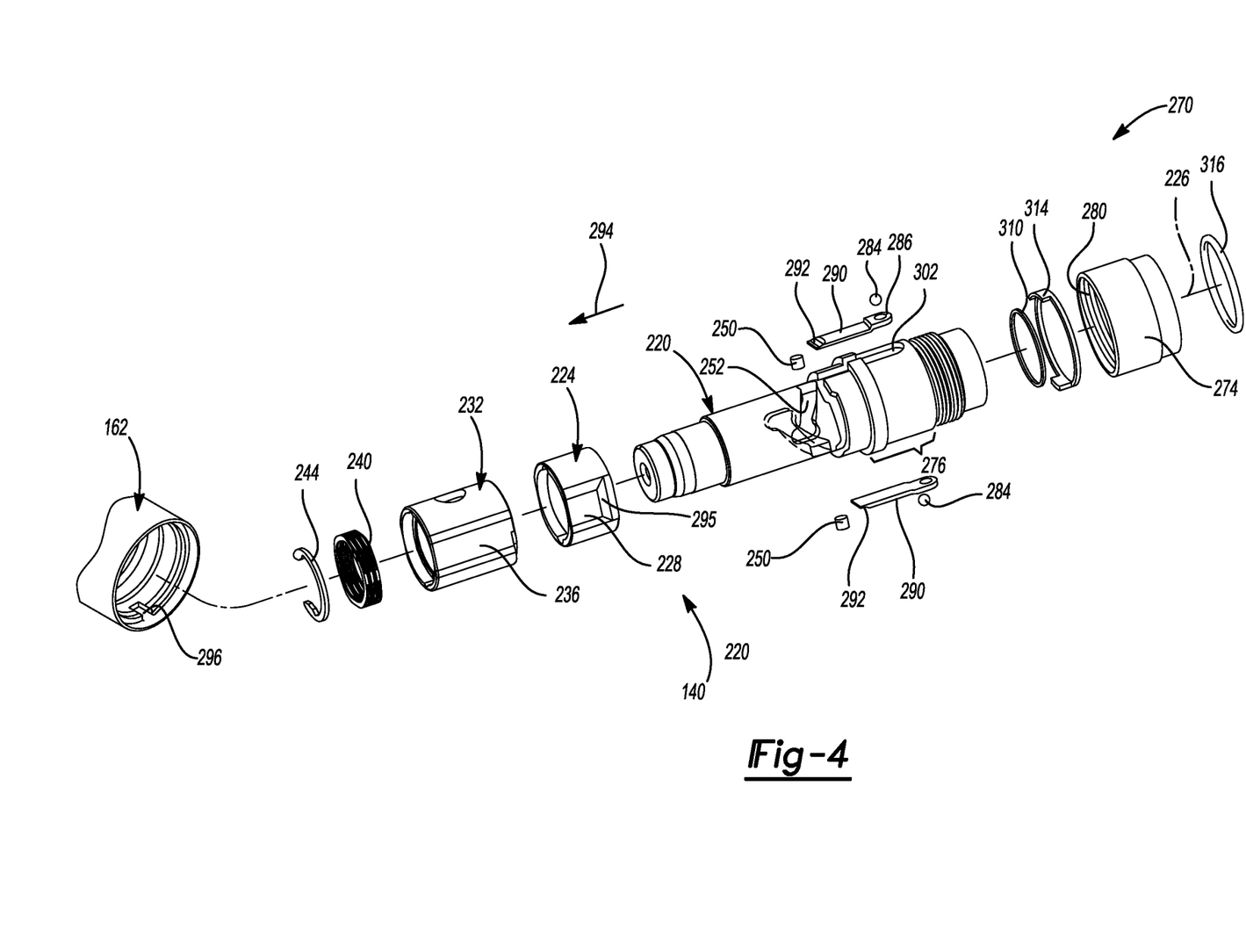
FIG. 4 is an exploded view of a secondary locking mechanism of an attachment to a collet, according to various embodiments.

Turning reference to FIG. 4, the collet assembly 140, according to various embodiments, is illustrated. The collet assembly 140 may include various internal components, such as the drive shaft, not illustrated here. It is understood that the internal components may be similar to those included in the Legend Stylus® powered motor assemblies sold by Medtronic, Inc. Therefore discussions of drive shaft details will not be included here. Nevertheless, the collet assemblies 140 may further include various external components. For example, the collet assemblies may include a collet housing 220 in which the various internal components may be positioned. The collet housing 220 may also include an external surface over which various components, including those discussed herein, may be positioned and moveable operated for various purposes.

As illustrated in FIG. 4, the collet assembly 140 including the collet housing 220 may include a first D-ring 224 that may rotate around a longitudinal axis 226 of the collet housing 220. The D-ring 224 may include an arcuate exterior with at least one flat region or portion 228. The flat portion 228, as discussed herein, may be engaged by an interior portion of the attachment 162 to rotate the first D-ring 224 between an unlocked and a locked position. The interior portion of the attachment 162 may include a protrusion 380 (FIG. 7) that extends from an internal surface of the attachment 162.

The collet assembly 140 may further include a second D-ring 232 that may also include an arcuate exterior surface and at least one flat portion 236. The second D-ring 232 may be rotationally fixed relative to the collet housing 220 such that it does not rotate relative to the longitudinal axis 226. The second D-ring 232, however, may move axially along the axis 226, Further, a wave spring 240 may be positioned between the second D-ring 232 and a locking portion, such as a snap ring 244. The snap ring 244 may engage a portion of the collet housing 220, such as a groove formed in the collet housing 220, to hold the snap ring 244 axially relative to the second D-ring 232. The wave spring 240 may bias the second d-ring 232 towards the motor engaging end 144 of the collet assembly 140.

As discussed herein, the attachment 162 may be fixed to the collet assembly 140 by sliding it over the flat portions 236 and 228, when they are aligned, and then rotating the attachment 162 to rotate at least the first D-ring 224 relative to the second D-ring 232. The spring force of the wave spring 240 against the second D-ring 232 may assist in holding the attachment 162 in place on the collet assembly 140.

Further, rotation of the attachment 162 may rotate the first D-ring 224. The attachment 162 may include an internal flat 380 (illustrated in FIG. 7) that engages the flat 228 of the first D-ring 224 to allow the attachment 162 to be rotated and rotate the first D-ring 224. In rotating the first D-ring 224 one or more fixation pins 250 may be moved in one or more J grooves 252. The pins 250, upon rotation of the first D-ring 224, may move in the J grooves 252 between a locked and an unlocked position. In various embodiments, rotations of the moves the pins 250 to a biased position in the locked position. Thus, an additional force to overcome the biased force is required to return the pins 250 (and therefore the attachment 162) to the original position. The rotation of the attachment 162 that rotates the first D-ring 224 may also lock and/or unlock internal components within the collet assembly 140. Therefore, the attachment 162 may assist in locking and unlocking both the attachment 162 and/or components within the collet assembly 140 such as the tool 170 positioned within the collet assembly 140.

The collet assembly 140, as discussed above, may engage the attachment 162. Also, as discussed above, the attachment 162 may be fixed to the collet assembly, at least in an axial direction, via an interaction with the first D-ring 224 and the second D-ring 232 at least upon rotation of the first D-ring 224 relative to the second D-ring 232. Upon releasing the attachment 162 the bias force of the wave spring 240 on the second D-ring 232 will engage the attachment 162 towards the motor attaching end 144 of the collet assembly. The attachment 162 may be rotationally held by interaction of the protrusion 380 with the flat 228 on the first D-ring 224.

The attachment 162 may be held axially relative to the collet 140 with the interaction with the first or second D-rings 224, 232, as discussed above. This connection (which may be a first attachment connection), however, may allow, due to various manufacturing tolerances, wear, etc., an amount of rotation, such as about 1 degree to about 5 degrees, of the attachment relative to the collet assembly 140. A supplemental or secondary locking system or feature 270, however, may also assist in rotational fixation and rigidity of the attachment 162 relative to the collet assembly 140.

The secondary locking system 270 may include, for example, various components such as a collar 274 that is able to rotate around the longitudinal axis 226. The collar 274 may be positioned over a portion, such as a collar accepting portion 276, of the collet housing 220. The collar 274 may include an internal helical groove 280 that may receive one or more locking balls 284. The balls 284 may be partially received within the helical groove 280 and further received within a receiving bore or depression 286 of a rotational locking member, such as a locking wedge 290. The locking wedge 290 may include a terminal end or distal end 292 that may move towards the second D-ring 232, generally in direction of arrow 294 (FIG. 4 and FIG. 6), to engage a rotational locking receiving seat or indent, such as a groove or depression 296 formed in an internal surface or end of the attachment 162 and/or a ramp surface 295 on the first D-ring 224.

Figure 5:
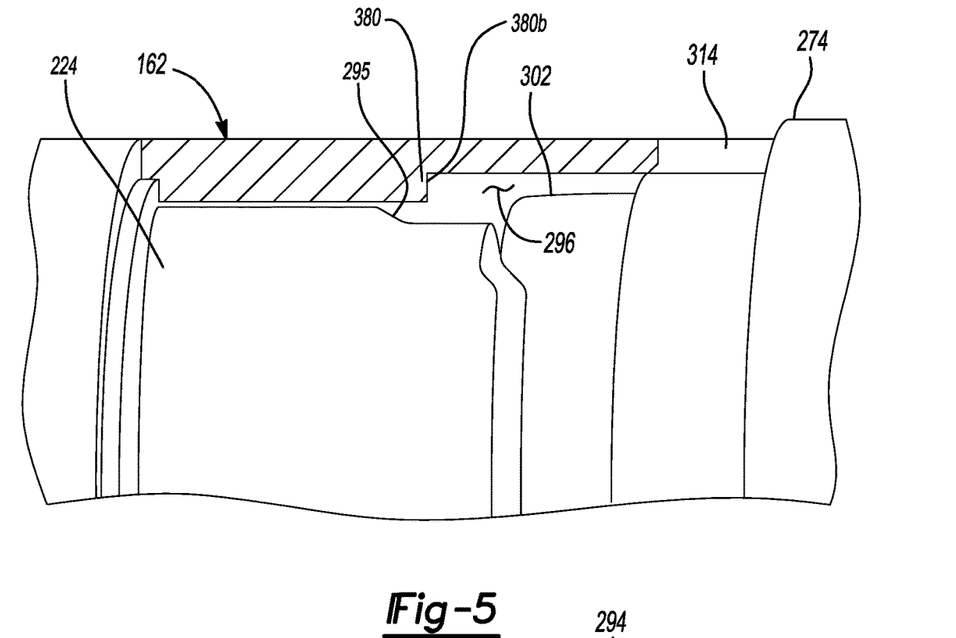
FIG. 5 is a detailed partial cross-sectional view of the secondary locking mechanism unengaged from the attachment.
Figure 6:
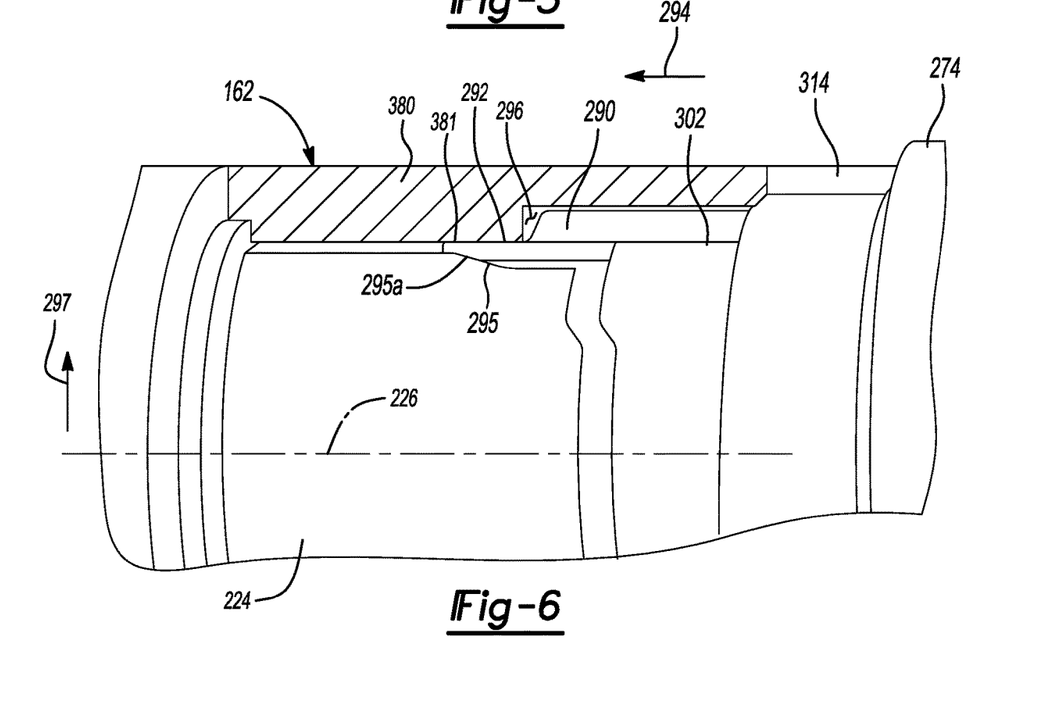
FIG. 6 is a detailed partial cross-sectional view of the secondary locking mechanism engaged to the attachment.

Briefly, and discussed further herein with reference to FIGS. 5 and 6, upon rotation of the collar 274 in a first direction, the balls 284 engaged in the groove 280 may move towards the second D-ring 232 moving the wedges 290 towards the second D-ring 232 and into the internal groove 296 of the attachment 162 and further to engage the ramp 295 of the first D-ring 224. When rotating the collar 274 in a second direction, the balls 284 in the groove 280 may move in a second direction away from the second D-ring 232 and, therefore, moving the wedges 290 away from the second D-ring 232 and out of the internal groove 296. It is understood, that only one wedge 290 and associated portions may be provided or more than two wedges 290 and associated portions may be provided. As illustrated, each of the wedges 290 may be positioned 180 degrees from one another.

The wedges 290 may ride in tracks or move in tracks or grooves 302 formed into an external surface of the collet housing 220. The grooves 302 may assist in moving the wedges 290 towards the second D-ring 232 and away from the second D-ring 232. The tracks 302 may also assist in guiding the wedges 290 towards the internal groove 296 to ensure proper engagement of the wedges in the grooves 296.

The secondary locking assembly 270 may further include additional portions such as a split ring 310. The split ring 310 may be between the collar 274 and the wedges 290. The split ring 310 assists in moving the wedges 290 in substantially parallel and tandem motion relative to the collet housing 220 and/or the attachment 162. A cover 314 may also be provided that is substantially stationary relative to at least a portion of the tracks or grooves 302. The cover 314 may cover a portion of the tracks 302 between the collar 274 and the attachment 162. Further, a friction plate or O-ring 316 may assist in holding the collar 274 onto the collet assembly 140, including the collet housing 220. It is understood that other appropriate portions may also be provided to assist in holding the collar 274 onto the collet housing 220.

Therefore, the secondary locking mechanism 270 is provided to assist in holding the attachment 162 substantially rotationally locked relative to the collet housing 220 when the attachment 162 is positioned on the collet assembly 140. In rotationally fixing or locking the attachment 162 relative to the collet assembly 140, the attachment 162 is also therefore rotationally fixed relative to the motor housing 100 and the tracking device 26. All or most possible rotational movement of the attachment 162 relative to the collet 140 is eliminated. Therefore, the secondary locking assembly 270 may assist in rotationally fixing the attachment 162 and/or the tool 170 relative to the motor housing 100 having the tracking device 26 fixed thereto. The secondary locking assembly 270, therefore, assists in or eliminates substantial rotational movement of the attachment 162 relative to the tracking device 26, 76. The amount of possible rotational motion may be limited to an amount that does not effect tracking or navigation to a selected preciseness for a selected procedure. Tracking may, therefore, be enhanced regarding the distal end 174 of the tool 170.

With additional reference to FIGS. 5 and 6, and continuing reference to FIG. 4, the secondary locking assembly 270 may engage and/or disengage the attachment 162. As illustrated in FIG. 5, the attachment 162 may be positioned on the collet assembly 140 in a selected manner, similar to how the attachment may be assembled on the collet assembly in a Legend Stylus® motor assembly sold by Medtronic, Inc. The attachment 162 may be positioned on the collet assembly 140 and be further engaged to the tool 170 for operation. Nevertheless, the secondary locking assembly 270 may not be engaged when the wedges 290 are not extended towards the second D-ring 232, as illustrated in FIG. 5. Accordingly, the wedges 290 of the secondary locking assembly 270 may not assist in resisting and/or eliminating rotational movement around the axis 226 by the attachment 162.

As illustrated in FIG. 6, however, the collar 270 has been rotated to move the wedges 290, including the distal ends 292, into the depressions or internal grooves 296 of the attachment 162. The wedge 290 may move in the direction of arrow 294 when the collar 274 is rotated to the locking position. The wedge 290 may continue to move and travel to engage the ramp 295 of the first D-ring 224. The wedge 290 may continue travel in the direction of arrow 294 after engaging the ramp 295, such that the wedge 290, including at least the distal end 292 moves away from the axis 226, such as in the direction of arrow 297. The wedge 290, including at least the distal end 292 may, therefore, contact a surface of the flat 380 of the attachment 162 and the ramp surface 295. The wedge 290, including the distal end 292, may then be wedged between the first D-ring 224 and the flat 380 of the attachment 162. By wedging, the wedge may contact a ramp surface 295a and a flat surface 381.

The wedge 290, therefore, may be axially positioned into the internal groove 296 of the attachment 162 and wedged between the ramp surface 295 first D-ring 224 (which may be an external surface of the collet assembly 140) and the attachment 162. The wedge 290 being in both the groove 296 and the groove 302 of the collet housing 220 and/or the wedging between the attachment 162 and the collet housing 220 may substantially rotationally lock the attachment 162 relative to the longitudinal axis 226. Therefore, the attachment 162 may be rotationally fixed relative to the collet housing 220 of the collet assembly 140 in addition to being axially fixed relative to the collet assembly 140. In either locked or unlocked configuration, the cover 314 may assist in concealing at least a portion of the groove 302.

Figure 7:
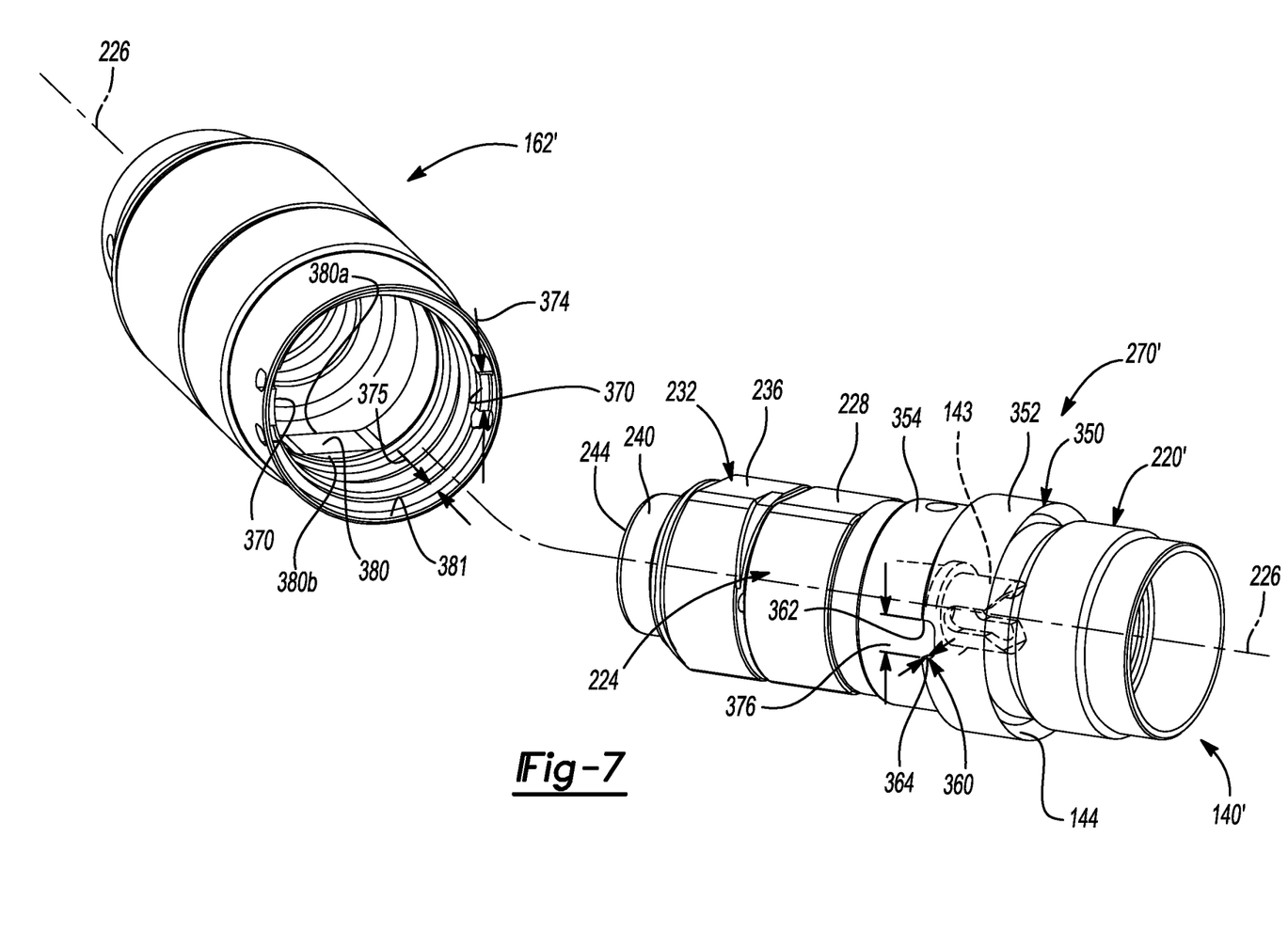
FIG. 7 is a perspective view of a secondary locking mechanism of an attachment and a collet, according to various embodiments.

Turning reference to FIG. 7, a collet assembly 140' is illustrated. The collet assembly 140' may include portions that are similar to the collet assembly 140, as discussed above. For example, collet assembly 140' may include the first D-ring 224 that includes the flat portion 228 and the second D-ring 232 having the second flat region or portion 236. Further the wave spring 240 and the snap ring 244 may be positioned in a collet assembly 140'. The collet assembly 140' may, however, include a collet housing 220' that is similar, that includes various different features from the collet housing 220 described above. The collet assembly 140', however, may also include the connection region 144 to engage the motor housing 100. Therefore, the collet assembly 140' may engage the motor housing 100 in a manner similar to that discussed above to form at least a collet to motor housing locking mechanism. The attachment 162' may also engage the collet assembly 140', as discussed below, in a manner similar to the attachment 162 engaging the collect assembly 140 with the first and second D-rings 232, 224. The connection of the attachment 162' to the collet 140' with the D-rings 224, 232 may form a first connection or locking system of the attachment 162' and the collet 140'

A supplemental or secondary locking system or feature 270' may be provided with the collet housing 220'. The secondary locking system 270' may include a collar or enlarged region 350 that has an external surface 352 that extends annularly above an adjacent external surface 354 of the collet housing 220'. Formed into the enlarged collar region 352 may be rotational locking receiving portions or seats, such as one or more indents 360. For example, two of the indents 360 may be formed substantially 180 degrees apart around the collar 350.

The indent 360 may include a sidewall 362. The sidewall 362 may extend away from the second D-ring 232 a selected distance, such as a distance 364. The distance 364 may be any appropriate distance, such as a distance of about 0.1 millimeters (mm) to about 5 mm. The distance 364, however, may be any appropriate distance to interact with a rotational locking member, such as a tab or detent 370 formed in an attachment 162'. The tab 370 may include a dimension appropriate to engage the indent 360. For example, the tab 370 may include a width 374 that is equal to or smaller than a width 376 of the indent 360. Therefore, the tab 370 may move into the indent 360. Upon positioning the tab 370 into the indent 360, the tab 370 may interfere or engage, such as by contact, the sidewall 362 upon rotational force between the attachment 162' and the collet housing 220'. Therefore rotational motion between the attachment 162' and the collet housing 220' may be limited and/or substantially eliminated, such as limiting rotation to less than 1 degree and/or 1 mm of travel around the axis 226.

The tab 370 may be formed at least by removing a portion of the internal surface of the attachment 162'. For example, through bores may be formed through the attachment 162' to form the tab 370. It is understood, however, that the tab 370 may be formed by removing material from an end of the attachment 162'. The tab 370 may have a height 375, therefore, once material is removed around the dimensions of the tab 370.

Also, any selected number of the tabs 370 may be formed. As illustrated, two of the tabs 370 may be formed substantially 180 degrees from each other. Other numbers of the tab 370, such as one or more than two may be provided.

A protective collar 381 may also extend beyond and end of the tab 370. The protective collar 381 may assist in eliminating or reducing possible damage to the tab 370. Thus, the tab 370 may have proper dimensions for engaging the indent 360.

Figure 8:
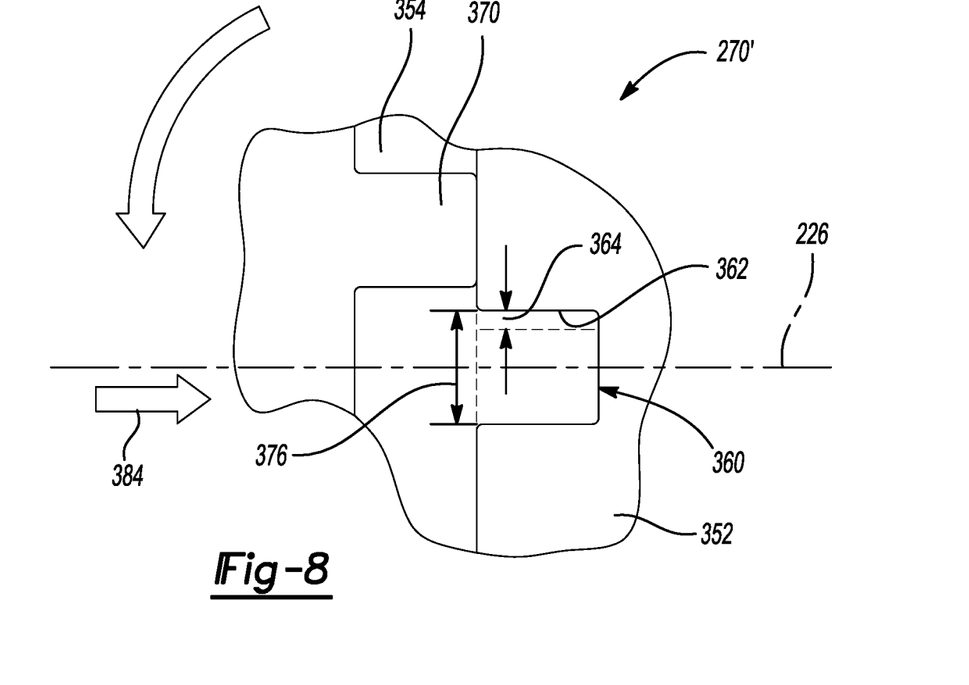
FIG. 8 is a detailed partial cross-sectional view of the secondary locking mechanism unengaged from the collet.

As discussed above the attachment 162' may include an internal structure, such as the flat or raised portion 380 that may pass over the flat portions 244 and 228 of the respective D-rings 232 and 224 in moving the attachment 162' towards the raised or enlarged collar 350. In the unlocked position, the tab 370 may not be aligned with the indent 360, as illustrated in FIG. 8. However, the attachment 162' may be moved in the direction towards the motor housing attachment 144 generally in the direction of arrow 384.

Figure 9:
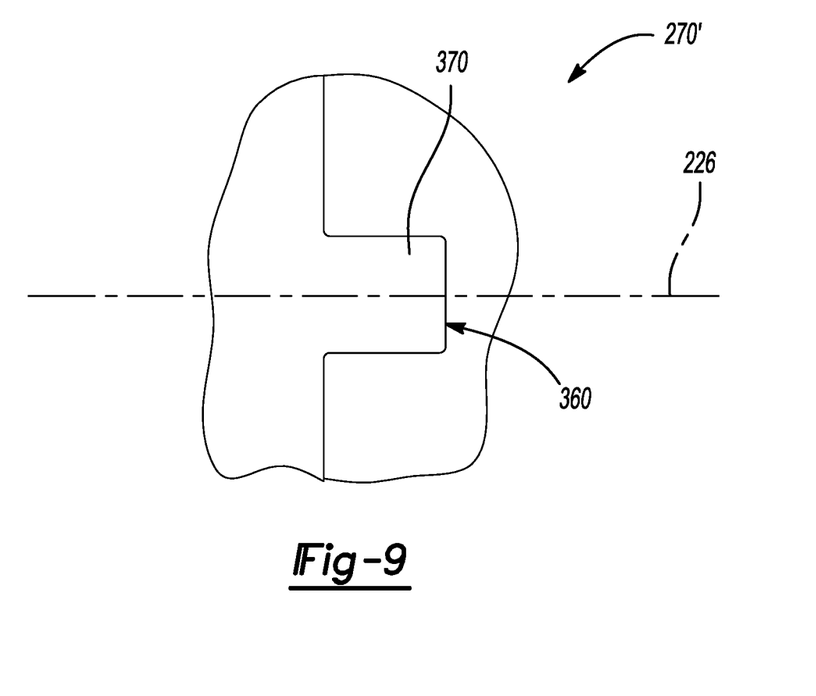
FIG. 9 is a detailed partial cross-sectional view of the secondary locking mechanism engaged to the collet.

The attachment 162' may then be rotated in a selected direction, such as around or about the longitudinal axis 226 of the collet assembly 140'. Upon rotation of the attachment 162' the first D-ring 224 may rotate relative to the second D-ring 232 and the attachment 162' may also rotate to align the tab 370 with the indent 362. Further axial motion of the attachment 162' will move the tab 370 into the indent 360, as illustrated in FIG. 9. Once the tab 370 is moved a selected distance into the indent 360, the first D-ring 224 may be fully rotated relative to the collet housing 220' to lock the attachment 162' onto the collet assembly 140' in an axial direction. The wave spring 244 may generally be pressing on the second D-ring 232 to bias the second D-ring 232 towards the connector 144. When the attachment 162' is rotated into the locked position, the second D-ring 232 is pressing on a surface 380a formed by protrusion 380 of the attachment 162'. Opposed to the surface 380a may be a second surface 380b, and when the second D-ring 232 is pressing on the surface 380a the attachment 162' is then being loaded and biased towards the collet housing shoulder 350. This load also causes the tab 370 to be biased towards and remain seated within the rotational locking seat, including the indent 360.

As discussed above, the first D-ring 224 may be engaged and move fixation pins 250 in the J grooves 252 to assist in locking the attachment 162, 162' onto the collet assembly 140' and/or the tool 170 into a drive shaft within the collet assembly 140'. Therefore rotation of the first D-ring 224 relative to the collet housing 220' may both move the first D-ring 224, the attachment 162', and internal mechanisms to lock the tool 170 onto the collet assembly 140'. Further, the movement and engagement of the tabs 370 into the indents 360 may further additional rotationally fix the attachment 162' to the collet assembly 140'. Again, as discussed above, rotationally fixing the attachment 162' to the collet assembly 140' may rotationally fix the attachment 162' relative to the motor housing 100 and eliminate substantial rotation of the attachment 162' relative to the tracking device 26, 76. Therefore, the tracking device 26 attached to the motor housing 100 may be rotationally and axially affixed to the collet assembly 140' and the attachment 162'. The tool 170, therefore, held within the attachment 162' and the collet assembly 140' may also be accurately tracked relative to the tracking device 26.

It is understood that any tracking device 26, 76 connected to the motor housing 100 can be axially fixed to the tool due to the axial and rotational fixation of the collet assembly 140, 140' to the motor housing 100 and the attachment 162, 162' to the motor housing 100 through the collet 140, 140'. Thus, accurate tracking of the tool 170 including the terminal end 174 may be properly made with the tracking system.

Figure 10A:
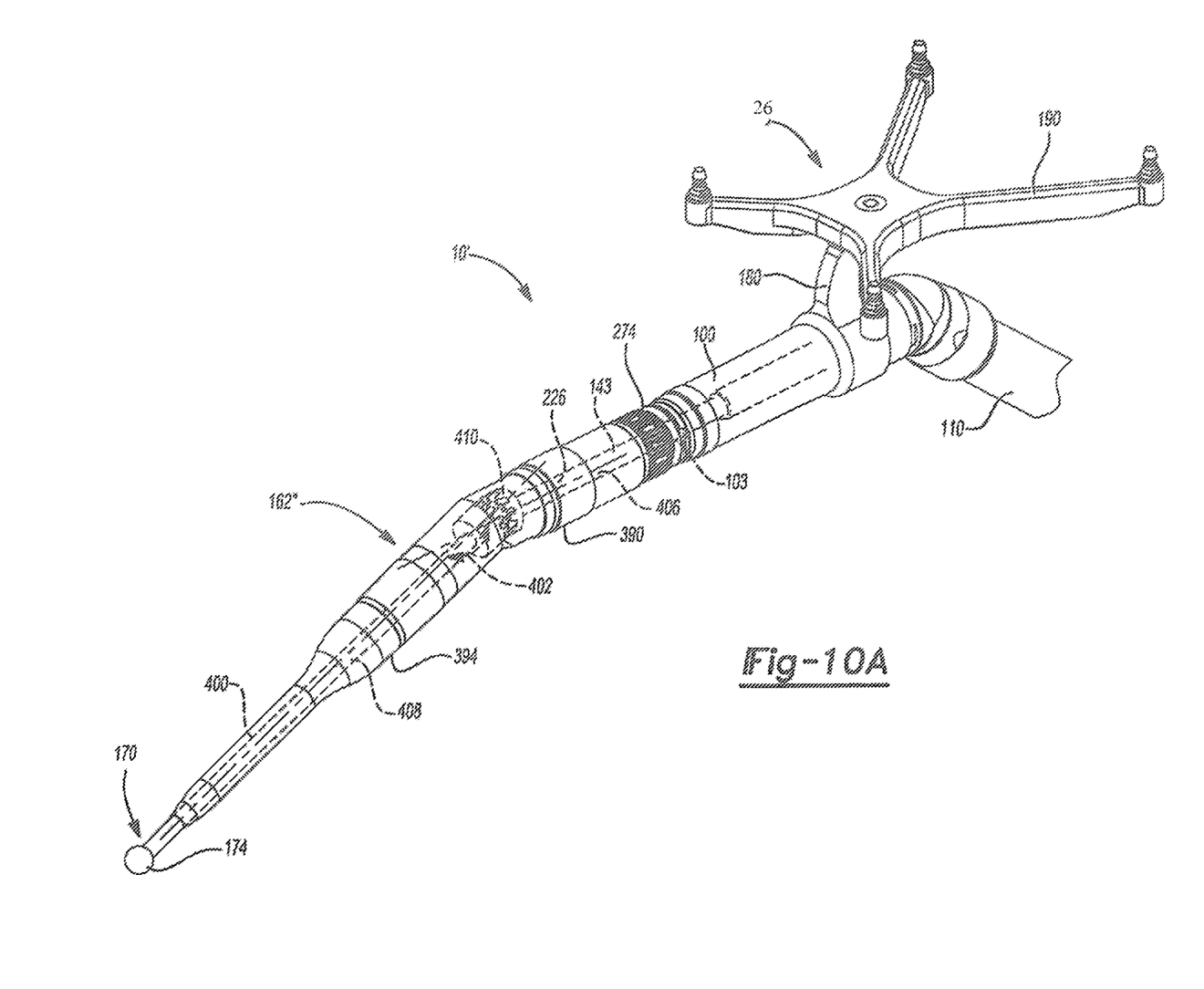
FIG. 10A is a perspective view of an attachment at a first orientation relative to a drill motor having secondary locking mechanism, according to various embodiments.
Figure 10B:
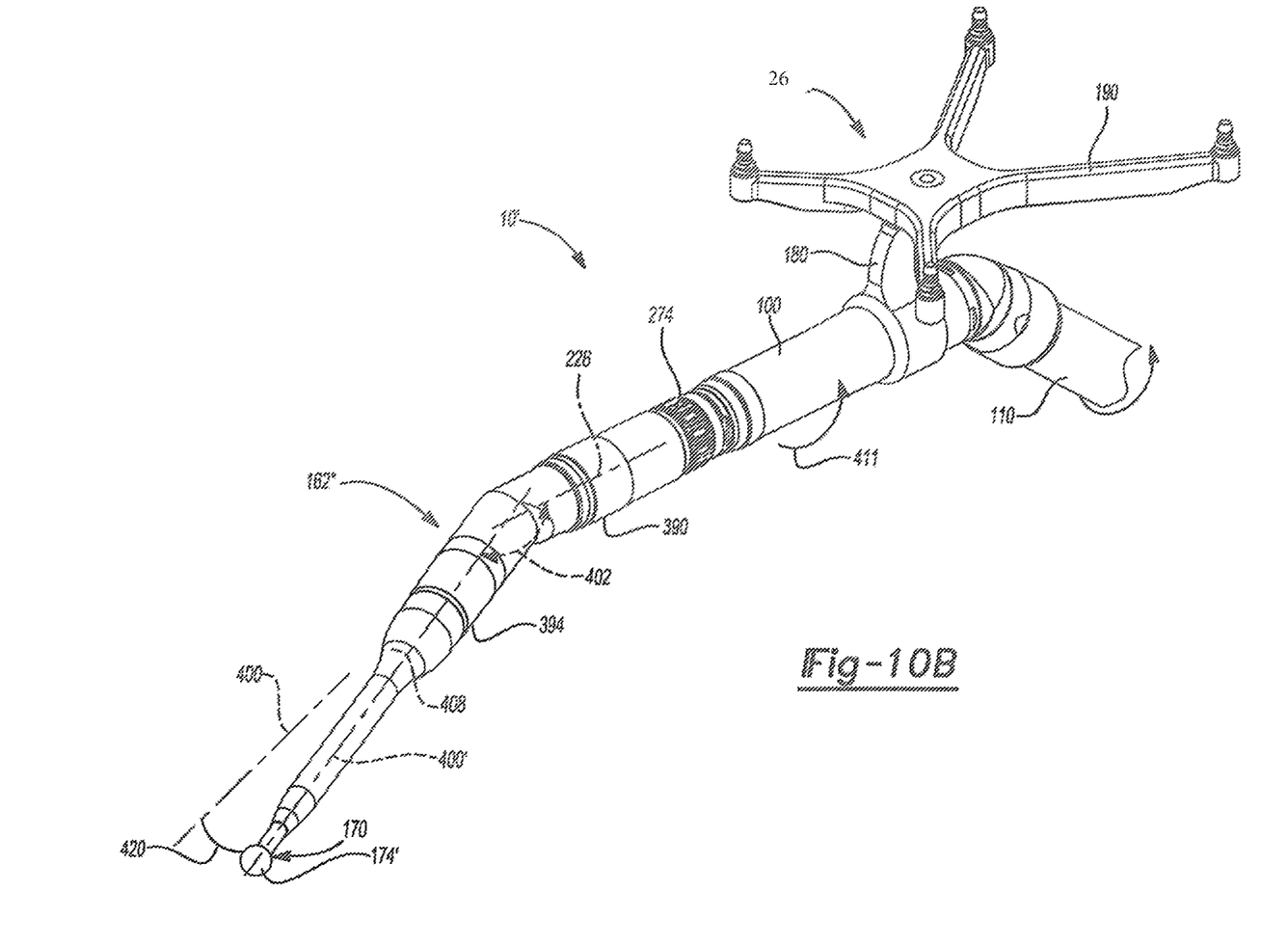
FIG. 10B is a perspective view of an attachment at a second orientation relative to a drill motor having secondary locking mechanism, according to various embodiments.

With reference to FIGS. 10A and 10B, a powered drill assembly 10' is illustrated. With initial reference to FIG. 10A the powered drill assembly 10' may include, according to various embodiments including those discussed above, the drill motor housing 100. Axially and rotationally rigidly affixed thereto is the tracking device 26 with the connector 180 connected to the array 190. The drill motor 101 within the housing 100 may be powered with the power source through the powerline 110, as discussed above. The drill motor housing 100 may be connected to the collet assembly 140 and/or the collet assembly 140' as discussed above. Therefore the collet assembly 140, 140' may be rotationally and axially fixed relative to the motor housing 100 and, therefore, the tracking device 26. As discussed above, the collet assembly 140, 140' may be fixed according to an appropriate mechanism, such as a threaded connection between the collet assembly 140, 140' and the motor housing 100.

The collet assembly may include the secondary attaching assembly or feature 270 including the collar 274, as exemplary as illustrated in FIG. 10A. It is understood that the secondary locking feature 270' may also or alternatively be provided, a discussion of the secondary locking feature 270 is used here for clarity of the current discussion.

Attached over the collet assembly 140 may be an attachment 162". The attachment 162" may include a first region 290 that extends along a longitudinal axis that, when connected to the motor housing 100, is coaxial with the axis 226. The axis 226 may be the central longitudinal axis of the motor housing 100. The attachment 162" may also include a second portion 394 that extends along the second axis 400. The second axis 400 may be formed at an angle 402 relative to the longitudinal axis 226. The angle 402 may be any appropriate angle such as about 1° to about 179°, or any appropriate angle. For example, the angle may be similar to the angle of angled attachment of the Legend Stylus® power drill assembly sold by Medtronic, Inc. The angle 402 may assist in positioning the tool 170, positioned within the angled attachment 162", at a selected angle or offset relative to the longitudinal axis 226 of the motor housing 100. The user 11 may suggest or use the offset to assist in performing a procedure on the subject 12. The angle 402 may assist in positioning the working end 174 of the tool 170 at a selected position for performing a procedure.

Nevertheless, according to various embodiments, the attachment 162" may be affixed to the drill motor housing 100 through the collet 140 such that the first axis 226 of the first portion 390 is substantially coplanar with the second axis 400 of the second portion 394. When the axes 226, 400 are coplanar, as illustrated in FIG. 10A and generally defined by the plane of the page, or at least in a first selected plane the position of the working end 174 relative to the tracking device 26 may be determined. Having the first axis 226 and the second axis 400 be coplanar may assist in a calibration of the working end 174 relative to the tracking device 26. Calibration may be an intra-operative calibration such as by the user 11 touching a known point with the working end 174, or may be predetermined such as during a manufacturing or assembly stage. During calibrating the tool 170 is positioned properly in the attachment 162" and the location of the tool 170, including the working end 174, may be determined relative to the tracking device 26.

Once the working end 174 is calibrated to the tracking device 26, the working end 174 may be tracked by the connection of the tracking device 26 to the motor housing 100 which is connected to the collet assembly 140, which is connected to the attachment 162", which is connected to the tool 170. The tool 170 may be driven through the angled attachment 162" via a first attachment drive shaft 406 that is coupled to a second attachment drive shaft 408 through an angled coupling 410. The first attachment drive shaft 406 may be attached through the collet drive shaft 143 to the motor drive shaft 103, as discussed above. Therefore the tool 170 may be driven at a position that is offset or angled relative to the longitudinal axis 226 of the drill motor housing 100.

As discussed above the secondary locking mechanism 270 may be operated to rotationally and rigidly fix the attachment 162" relative to the collet assembly 140, and, therefore, to the motor housing 100 having the tracking device 26 fixed thereto. Therefore, the secondary locking mechanism 270 may rigidly rotationally fix the attachment 162" relative to the tracking device 26 that is mounted on the drill motor housing 100.

Turning reference to FIG. 10B, the angled attachment 162", if not rotationally fixed relative to the motor housing 100, may rotate from a selected position, as discussed above. As illustrated in FIG. 10A, the second axis 400 may be selectively substantially coplanar with the first axis 226. If the attachment 162" rotates, such as in the direction of arrow 411, around the axis 226, then the axis 400 of the second portion 394 may move to a rotated position 400' that is not at the same position as the axis 400, which is coplanar with the axis 226.

In FIG. 10B, the axis 400' is understood to be extending out of the page and is no longer coplanar with the axis 226. Therefore, rotation may impart a rotational or angular error 420 between the predetermined and/or calibrated position of the working end 174 to an angled or error position 174' relative to the coplanar or calibrated axis position 400. The secondary locking mechanism 270 may be used to ensure rotationally rigid fixedness of the attachment 162" relative to the motor housing 100, and, therefore, the tracking device 26. It is understood that the secondary attachment 270 may be an appropriate secondary attachment, including both the secondary attachment 270 and the secondary attachment 270'.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of connecting a powered drill assembly to track a tool tip powered by the powered drill, comprising:
    connecting a collet assembly having a powered drill motor housing connection configured to fixedly engage a second end of a powered drill motor housing, wherein the powered drill motor housing connection rigidly fixes the collet assembly with the powered drill motor housing;
    positioning at least a portion of the collet assembly within a bore formed by an internal surface of an attachment member to at least in part form a first locking feature; and
    engaging a secondary locking feature configured to at least limit rotational movement of the attachment member relative to the collet assembly;
    wherein a tracking device is fixed relative to an exterior surface of the powered drill motor housing, wherein the tracking device is configured to allow tracking of the powered drill assembly,
    wherein engaging the secondary locking feature includes:
        moving a protrusion extending from the internal surface of the attachment member past a wave spring positioned on a collet housing; and
        releasing the attachment member to allow the wave spring to bias a tab formed on the internal surface of the attachment member into an indent formed in the collet housing.

2. The method of claim 1, further comprising: tracking the tool tip with the tracking device.

3. The method of claim 2, further comprising:
    eliminating substantial rotation of the tracking device relative to the attachment member at least with the engagement of the secondary locking feature.

4. The method of claim 3, further comprising:
    fixing the tracking device to the exterior surface of the powered drill motor housing.

5. The method of claim 3, further comprising:
    operating a tracking system to track the tool tip.

6. The method of claim 1, wherein engaging the secondary locking assembly includes:
    moving a wedge by rotating a collar of the collet assembly into a first groove formed in the collet housing and into a second groove formed in the internal surface of the attachment member, wherein upon moving the wedge, the wedge is configured to wedge between the internal surface of the attachment member and an external surface of the collet assembly.

7. The method of claim 1, wherein engaging the secondary locking feature includes moving a rotational locking member into a rotational locking seat.

8. A method of connecting a powered drill assembly to track a tool tip powered by the powered drill, comprising:

connecting a collet assembly having a powered drill motor housing connection configured to operably engage a powered drill motor housing;

positioning at least a portion of the collet assembly within a bore formed by an internal surface of an attachment member to form a first locking feature;

engaging a secondary locking feature configured to limit rotational movement of the attachment member relative to the collet assembly, wherein engaging the secondary feature includes:

moving a wedge by rotating a collar of the collet assembly into a first groove formed in the collet housing and into a second groove formed in the internal surface of the attachment member, wherein upon moving the wedge into the second groove, the wedge biases between the internal surface of the attachment member and an external surface of the collet assembly; and engaging a tracking device to an exterior surface of the powered drill motor housing, the tracking device configured to allow tracking of the powered drill assembly.

9. A method of connecting a powered drill assembly to track a tool tip powered by the powered drill, comprising:

connecting a collet assembly having a powered drill motor housing connection configured to operably engage a powered drill motor housing;

positioning at least a portion of the collet assembly within a bore formed by an internal surface of an attachment member to form a first locking feature;

engaging a secondary locking feature configured to limit rotational movement of the attachment member relative to the collet assembly, wherein engaging the secondary locking feature includes:

moving a protrusion extending from the internal surface of the attachment member past a wave spring positioned on a collet housing; and     releasing the attachment member to allow the wave spring to bias a tab formed on the internal surface of the attachment member into an indent formed in the collet housing; and engaging a tracking device to an exterior surface of the powered drill motor housing, the tracking device configured to allow tracking of the powered drill assembly.

\* \* \* \* \*